United States Patent [19]

Hull et al.

[11] 4,379,781

[45] Apr. 12, 1983

[54] ANTIBIOTIC COMPOSITIONS

[75] Inventors: Robert N. Hull, Greenwood; Robert S. Gordee, Indianapolis, both of Ind.

[73] Assignee: Eli Lilly and Company, Indianapolis, Ind.

[21] Appl. No.: 241,809

[22] Filed: Mar. 9, 1981

Related U.S. Application Data

[63] Continuation-in-part of Ser. No. 107,239, Dec. 26, 1979, abandoned.

[51] Int. Cl.³ ............................................. A61K 35/00
[52] U.S. Cl. .................................................. 424/114
[58] Field of Search ........................................ 424/114

[56] References Cited

U.S. PATENT DOCUMENTS

| | | | |
|---|---|---|---|
| 3,178,341 | 4/1965 | Hamill et al. | 424/120 |
| 3,491,187 | 1/1970 | Ely | 424/181 |
| 3,691,279 | 9/1972 | Thompson et al. | 424/116 |

OTHER PUBLICATIONS

Associated Biomedio Systems, Inc., Catalogue, p. 10.
Chemical Abstracts 84:84801 G (1976).
The Merck Index, 9th Ed. (1976), pp. 230, 565, 714, 887, 1131, 1260 and 1261.
Schering Diagnostics, "Gentamycin" *Advertising Literature.*
Micro Biological Assoc., Inc., Advertising Literature Titled "The Ideal Antibiotic" and Gentamicin.
French Republic Search Report.
N. Shishkov and D. Droumev, "Possibilities for Synergic Action of Some Drug Combinations Against Mycoplasma Gallisepticum," Proc. Int. Congr. Chemother., 8th 1973 (Publ. 1974) 1, 356–361 (Eng.) Ed. by Daikos, G. K., *Hell. Soc. Chemother.*: Athens, Greece.

*Primary Examiner*—Jerome D. Goldberg
*Attorney, Agent, or Firm*—William B. Scanlon; Arthur R. Whale

[57] ABSTRACT

Macrolide antibiotics tylosin, spiromycin, cleandomycin, magnamycin, and leucomycin in combination with aminoglycoside antibiotics tobramycin, apramycin, nebramycin 5, gentamicin and neomycin form synergistic compositions which inhibit the growth of mycoplasma in mammalian tissue cultures. Tylosin-apramycin compositions enhance the feed efficiency and weight gain in post weaned pigs and are useful in the control of *Pasturella hemolytica* an infectious organism in cattle.

3 Claims, No Drawings

ANTIBIOTIC COMPOSITIONS

CROSS REFERENCE TO RELATED APPLICATIONS

This application is a continuation-in-part of application Ser. No. 107,239 filed Dec. 26, 1979 now abandoned.

SUMMARY OF THE INVENTION

This invention relates to antibiotic combinations. In particular it relates to antibiotic combinations comprising certain macrolide antibiotics and certain aminoglycoside antibiotics which possess synergistic activity against mycoplasma.

Antibiotic combinations of the invention comprise a macrolide antibiotic e.g., tylosin and spiromycin in combination with one of the following aminoglycoside antibiotics: tobramycin, apramycin, neomycin, gentamicin, and nebramycin factor 5. The compositions of the invention are particularly useful in controlling the growth of resistant mycoplasma in tissue culture media.

Preferred antibiotic compositions of this invention comprise tylosin and tobramycin or apramycin. The preferred composition of this invention comprising tylosin and apramycin is also useful in the treatment of post weaning colibacillosis in pigs when administered in the animals feed or drinking water as disclosed in copending application Ser. No. 107,240, filed Dec. 26, 1979 now U.S. Pat. No. 4,283,388 issued Aug. 11, 1981. Further, the preferred tylosin-apramycin compositions enhances the growth and feed efficiency in weaned pigs.

DETAILED DESCRIPTION

The antibiotic compositions provided by this invention comprise a macrolide antibiotic and an aminoglycoside antibiotic in a synergistically effective concentration. Macrolide antibiotics which are employed in the compositions are tylosin, spiromycin, magnamycin (also known as carbomycin A), leucomycin, and oleandomycin. Aminoglycoside or aminocyclitol antibiotics which are used in combination with one of the above macrolides are tobramycin, apramycin, nebramycin 5, gentamicin, and neomycin.

The macrolide and aminoglycoside antibiotics comprising the compositions are all known. Tylosin, U.S. Pat. No. 3,178,341, Merck Index 9th Ed., No. 9486 is sold commercially as a veterinary antibiotic; spiromycin is disclosed in U.S. Pat. No. 2,943,023, Merck Index 9th Ed., No. 8525; leucomycin is disclosed in Merck Index 9th., No. 5307; magnamycin is disclosed in U.S. Pat. No. 2,960,438 and Merck Index 9th Ed., No. 1812 and oleandomycin is disclosed in U.S. Pat. Nos. 2,757,123 and 2,842,481 and Merck Index 9th Ed., No. 6671.

The aminoglycoside antibiotics tobramycin and apramycin are alternatively known as nebramycin factors 6 and 2 respectively. Tobramycin, apramycin and nebramycin factor 5 are members of the nebramycin complex of antibiotics produced by *Streptomyces tennibrarius* and are described in U.S. Pat. No. 3,691,279. Tobramycin is used clinically in human medicine. Neomycin is disclosed in U.S. Pat. No. 2,799,620 while gentamicin, a clinically useful antibiotic in human medicine, is disclosed in U.S. Pat. No. 3,091,572 and Merck Index 9th Ed., No. 4223.

The antibiotic compositions of this invention are useful in the control of mycoplasma and in particular mycoplasma that are resistant to the individual antibiotics. The synergism of the compositions was demonstrated in mammalian tissue cultures where mycoplasma are frequent and often unrecognized contaminants. The mycoplasma contamination of tissue culture preparations of various cell lines, for example in the propagation of animal virus, can ruin the culture preparation and is some instances after culture has been maintained for several weeks. The synergistic activity of the compositions of this invention is best demonstrated against resistant mycoplasma in mammalian tissue culture. The term, "resistant mycoplasma," as used herein refers to mycoplasma which are resistant to both the macrolide antibiotics and the aminoglycoside antibiotics comprising the compositions of this invention at minimal inhibitory concentrations higher than those generally observed with the antibiotics against various microorganisms. A number of mycoplasma are resistant to the antibiotics comprising the compositions of this invention. Prevalent among resistant mycoplasma contaminants in mammalian tissue culture preparations are strains of *M. hyorhinis*. *M. gallisepticum* resistant strains are also frequent contaminants. The synergistic compositions of this invention inhibit the growth of resistant mycoplasma microorganisms at low concentrations when the individual antibiotics are ineffective alone at high concentrations. The following TABLE 1 lists the minimal inhibitory concentrations (MIC) in mcg./ml for the individual macrolide and aminoglycoside antibiotics and their combinations. The MIC values were obtained with mammalian tissue cultures contaminated with the designated mycoplasma in experiments carried out as follows.

Suspensions of monkey kidney cells, LLC-MK2, in Medium 199 (Morgan et al., Proc. Soc. Exp. Bio. Med, 73, 1 1950), were inoculated with cultures of the indicated mycoplasma to achieve an inoculum concentration of $1.5 \times 10^7$ organisms/ml of cell suspension. Control cultures and the mycoplasma positive cultures included in each test were incubated at 37° C. for 3-5 days. After incubation the medium in all cultures was changed to 1% horse serum in Medium 199 containing 1.68 g of sodium bicarbonate per liter. The tissue cultures innoculated with mycoplasma (except for mycoplasma positive control cultures) were then treated with the indicated individual antibiotics alone or with the combination of antibiotics shown in TABLE 1. When combinations of antibiotics were tested equal amounts of the antibiotics were used.

Solutions of the antibiotics were made up in Medium 199 containing 1.68 g of sodium bicarbonate per liter of medium. The solutions were sterile filtered through a millipore filter having a 0.2 micron porosity and were stored at 4° C. prior to use. Two fold dilutions of the antibiotic solutions were made and each antibiotic solution was added to separate cultures to determine the minimal inhibitory concentration. The medium in each culture was changed twice a week with fresh antibiotic solution at the same concentration being added at each medium change. After two weeks, medium changes were made without antibiotic for two more weeks. Samples of the cultures were taken before each medium change in the last two weeks and were cultured to determine the presence of mycoplasma.

TABLE 1

MINIMAL INHIBITORY CONCENTRATIONS OF ANTIBIOTICS vs MYCOPLASMA IN LLC-MK2 TISSUE CULTURE

| Antibiotic[1] | Mycoplasma | Minimal Inhibitory Concentration (mcg/ml) |
|---|---|---|
| Tylosin | M. Hyorhinis HH[2] | >250 |
| Tobramycin | M. Hyorhinis HH[2] | 62.5 |
| Combination | M. Hyorhinis HH[2] | <15.6 |
| Tylosin | M. Hyorhinis | 100 |
| Tobramycin | M. Hyorhinis | 100 |
| Combination | M. Hyorhinis | 3 |
| Tylosin | M. Hyorhinis HEK[3] | >200 |
| Tobramycin | M. Hyorhinis HEK[3] | >500 |
| Combination | M. Hyorhinis HEK[3] | 3.1 |
| Tylosin tartrate | M. Hyorhinis HH | 200 |
| Tobramycin sulfate | M. Hyorhinis HH | 200 |
| Combination | M. Hyorhinis HH | 1.5 |
| Tylosin tartrate | M. gallisepticum 36 F[4] | >800 |
| Tobramycin | M. gallisepticum 36 F[4] | 100 |
| Combination | M. gallisepticum 36 F[4] | 25 |
| Tylosin | M. gallisepticum 41313[5] | 800 |
| Tobramycin | M. gallisepticum 41313[5] | 200 |
| Combination | M. gallisepticum | 12.5 |
| Tylosin | Swine L3F12F7[6] | 200 |
| Tobramycin | Swine L3F12F7[6] | 50 |
| Combination | Swine L3F12F7[6] | <1.5 |
| Tylosin | M. Hyorhinis HH | 200 |
| Apramycin | M. Hyorhinis HH | 600 |
| Combination | M. Hyorhinis HH | 12 |
| Tylosin | M. Hyorhinis | 400 |
| Gentamicin | M. Hyorhinis | 100 |
| Combination | M. Hyorhinis | 0.78 |
| Tylosin | M. Hyorhinis HH | >800 |
| Nebramycin Factor 5 | M. Hyorhinis HH | 200 |
| Combination | M. Hyorhinis HH | 25 |
| Tylosin | M. Hyorhinis | 200 |
| Neomycin | M. Hyorhinis | 100 |
| Combination | M. Hyorhinis | 6.3 |
| Spiromycin | M. Hyorhinis HH | 800 |
| Tobramycin | M. Hyorhinis HH | 200 |
| Combination | M. Hyorhinis HH | 1.5 |
| Magnamycin | M. Hyorhinis HH | >800 |
| Tobramycin | M. Hyorhinis HH | 200 |
| Combination | M. Hyorhinis HH | 1.5 |
| Leucomycin | M. Hyorhinis HH | 400 |
| Tobramycin | M. Hyorhinis HH | 200 |
| Combination | M. Hyorhinis HH | 0.78 |
| Oleandomycin | M. Hyorhinis HH | >400 |
| Tobramycin | M. Hyorhinis HH | 200 |
| Combination | M. Hyorhinis HH | 100 |

[1]Combinations of the indicated antibiotics contained equal amounts of each antibiotic.
[2]M. hyorhinis H.H. is an isolate from human heart tissue
[3]M. hyorhinis HEK is an isolate from human embryonic kidney tissue
[4]M. gallisepticum 36F is a strain of a chicken mycoplasma
[5]M. gallisepticum 41313 is a strain of a chicken mycoplasma
[6]Swine L3F12F7 was a mycoplasma isolated from swine and from its characteristics appears to be Mycoplasma arginini As is shown in Table 1 the mycoplasma employed in the test were controlled only at high concentrations by the individual antibiotics. However when one of the macrolide—aminoglycoside compositions of this invention was used the mycoplasma were controlled at greatly reduced concentrations. In each combination the individual antibiotics were present in equal parts.

The compositions of this invention are non-toxic to mammalian tissue and can be used to maintain cell lines free of contamination by mycoplasma. The compositions can also be used in conjunction with other antibiotics which are commonly used in tissue cultures to prevent bacterial contamination but which are ineffective in controlling mycoplasma. For example the synergistic compositions can be used with a penicillin such as penicillin G or with streptomycin, two antibiotics commonly used in tissue cultures.

A preferred composition of this invention is tylosin-tobramycin. This composition has consistently exhibited low minimal inhibitory concentrations against mycoplasma which tylosin or tobramycin alone control only at high minimal inhibitory concentrations. Table 2 which follows contains the results obtained with numerous combinations of tylosin and tobramycin which inhibited the growth of M. hyorhinis in tissue culture preparations using monkey kidney cells LLC-MK2. The tests were conducted in the following manner.

Tissue cultures of LLC-MK2 cells were inoculated with M. hyorhinis culture five days prior to the addition of tylosin-tobramycin combinations containing varying proportions of the antibiotics and at various concentrations. Medium changes were made at three to five-day intervals with antibiotics addition at each change. Samples of the culture media were taken at each media change and assayed for mycoplasma. The data in Table 2 illustrate various proportions of the antibiotics in combinations which inhibited the growth of M. hyorhinis.

TABLE 2

Inhibition of M. hyorhinis in LLC-MK2 Tissue Culture by Tylosin-Tobramycin Compositions

| Tobramycin (mcg/ml) | plus | Tylosin (mcg/ml) |
|---|---|---|
| 12 | | 1 |
| 6 | | 1 |
| 3 | | 1 |
| 2 | | 2 |
| 1 | | 6 |
| 0.5 | | 12 |

All of the combinations of tylosin and tobramycin shown in Table 2 inhibited the growth of mycoplasma for from five to eight samplings covering a period of three and a half weeks. When used alone tylosin and tobramycin exhibit much higher MIC values as shown in Table 1.

The data in Table 2 demonstrate the low concentrations at which the antibiotic compositions of this invention are synergistically effective. Compositions containing from about one part of tobramycin or greater to about 3 parts of tylosin or greater by weight are preferred synergistic compositions.

Another preferred composition of this invention comprises tylosin in combination with apramycin. As is shown in Table 1, the solution containing 12 mcg/ml of tylosin and 12 mcg/ml of apramycin inhibited mycoplasma whereas the MIC for apramycin alone was 600 mcg/ml and that for tylosin alone was 200 mcg/ml.

A further preferred composition comprises tylosin in combination with gentamicin.

In contrast to the synergism demonstrated by the macrolide antibiotic-aminoglycoside antibiotic compositions of this invention a number of macrolide-macrolide antibiotic combinations showed little if any enhanced activity in the control of mycoplasma in tissue cultures.

The macrolide and aminoglycoside antibiotics forming the synergistic compositions can be in a suitable acid addition salt form or as the free bases. These antibiotics form salts with mineral acids and carboxylic acids. Examples of such salts are tylosin hydrochloride, tylosin tartrate, tylosine phosphate, spiromycin adipate, spiromycin hydrochloride, oleandomycin hydrochloride, leucomycin hydrobromide, magnamycin tartrate, tobramycin sulfate, apramycin hydrochloride, neomycin sulfate, neomysin hydrochloride, gentamicin hydrochloride, and gentamicin sulfate.

The antibiotic formulations of this invention can be prepared by mixing the dry antibiotic powders of the free base or a salt form thereof or, alternatively solutions of the antibiotics of the appropriate concentration can be mixed to obtain a solution of the two antibiotics of the desired concentration. The individual antibiotics are appreciably soluble in aqueous media and solutions of the formulations in aqueous tissue culture medium are desirably used in controlling mycoplasma contamination in mammalian tissue cultures.

The synergistic antibiotic compositions of this invention can be used to inhibit the growth of mycoplasma in a wide variety of mammalian tissue and thus prevent the contamination and loss thereof. For example, a composition of the invention can be employed in mammalian tissue cultures used in the preparation of plasminogen activator according to the method described by Hull et al., U.S. Pat. No. 3,904,480.

The antibiotic compositions of this invention comprise the macrolide antibiotic in the ratio by weight to the aminoglycoside antibiotic of from about 15:1 to about 1:15. A preferred ratio by weight of the macrolide to the aminoglycoside is about 3:1 to about 1:3.

A preferred antibiotic composition of this invention, tylosin in combination with apramycin, is also useful in enhancing the growth in past weaned pigs. The tylosin-apramycin combination demonstrates higher feed utilization and higher weight gains in post weaned pigs than does either antibiotic when administered alone. The efficacy of the tylosin-apramycin combination in enhancing feed utilization and weight gain in post weaned pigs was determined in animal trials carried out as follows.

The trials were carried out in pens with 6 pigs per pen for 28 days. The pigs were of mixed sex having an average initial body weight of 12.89 kg. and an average age of six weeks. The animals received water before and after feeding. The animals were fed twice daily with feed having the following composition.

| Ingredient | Percent |
|---|---|
| Wheat | 21 |
| Barley | 23.5 |
| Corn | 20 |
| Fish meal | 2.5 |
| Yeast | 1 |
| Wheat bran | 10 |
| Alfalfa | 2.5 |
| Soybean meal | 14 |
| Oat hulls | 1.8 |
| Calcium phosphate | 1 |
| Calcium carbonate | 1.1 |
| Sodium Chloride | 0.1 |
| Premix SV12 | 1 |
| Premix SO4 | 0.5 |

The tylosin-apramycin combination was compared in the trials with tylosin alone and with apramycin alone. The antibiotics and the combination thereof were administered in the animal feed at a level of 100 ppm, and, in the case of the combination; at 100 ppm for each antibiotic.

The combined results of two like trials are shown below in TABLE 3.

TABLE 3

Comparative Weight Gains And Feed Utilization in Pigs Treated With Apramycin - Tylosin, Tylosin And Apramycin

| Treatment | | Negative Control | Tylosin | Apramycin | Tylosin - Apramycin |
|---|---|---|---|---|---|
| Conc. in Feed (ppm) | | — | 100 | 100 | 100–100 |
| Number of animals n | | 70 | 71 | 72 | 72 |
| Number of replic. n | | 12 | 12 | 12 | 12 |
| Initial weight | $\bar{x}$ | 13,11 | 13,03 | 12,55 | 12,85 |
| (kg) per animal | ±s | 0,81 | 1,04 | 0,58 | 0,71 |
| | v | 6 | 8 | 5 | 6 |
| | (Rel) | (100) | (99) | (96) | (98) |
| Final weight | $\bar{x}$ | 25,00 | 25,58 | 25,62 | 26,71 |
| (kg) per animal | ±s | 1,48 | 1,65 | 1,14 | 1,49 |
| | v | 6 | 6 | 4 | 6 |
| | (Rel) | (100) | (102) | (102) | (107) |
| Daily gain | $\bar{x}$ | 425 | 449 | 467 | 495 |
| (g) per animal | ±s | 40 | 62 | 38 | 44 |
| | v | 9 | 14 | 8 | 9 |
| | (Rel) | (100) | (106) | (110) | (116) |
| Daily feed in- | $\bar{x}$ | 0,92 | 0,92 | 0,92 | 0,94 |
| take (kg) per | ±s | 0,06 | 0,06 | 0,04 | 0,05 |
| animal | v | 7 | 6 | 4 | 5 |
| | (Rel) | (100) | (100) | (100) | (102) |
| Feed efficiency | $\bar{x}$ | 2,14 | 2,07 | 1,96 | 1,90 |
| (kg feed/kg | ±s | 0,10 | 0,17 | 0,09 | 0,09 |
| gain) | v | 4 | 8 | 4 | 5 |
| | (Rel) | (100) | (97) | (92) | (89) |

In Table 3 the statistical symbols have the following meanings: X=means; ±s=standard deviation; v=coefficient of variances; and (Rel.)=comparison treatments to negative controls in percentage.

As shown in TABLE 3 the pigs treated with tylosin-apramycin combination showed higher weight gains and better feed efficiency on the 28 day trial than did the pigs treated with tylosin alone or with apramycin alone.

The tylosin-apramycin compositions of this invention demonstrate synergistic activity against strains of Pasturella hemolytica. This organism can cause pneumonia in cattle which in cases of severe infection can lead to death. The synergism of the tylosin-apramycin combination was demonstrated in vitro against P. hemolytica strain 41D. Tylosin alone had a minimal inhibitory concentration of 50 mcg/ml and that for apramycin alone was 25 mcg/ml. The synergistic activity of the combination of the two antibiotics was determined by the "checkerboard" titration method. In this method two antibiotics are tested in serial dilutions and in all combinations of these dilutions together to find the concentrations of each antibiotic, both alone and in combination, that inhibit growth of the test microorganism. The nature of the interaction between the two antibiotics may be determined algebraically or geometrically. In the algebraic method, the concentration of each antibiotic in the combination that inhibits growth is expressed as a fraction of the concentration that produces the same effect when the antibiotic is used alone. When the sum of these fractions is one, the combination is additive; when the sum is less than one, the combination is synergistic; and when the sum is greater than one, the combination is antagonistic.

Below are shown the calculations using data obtained in the vitro test of tylosin, apramycin and the combination of the two antibiotics against P. hemolytica.

Tylosin alone: MIC=50 mcg/ml
apramycin: MIC=25 mcg/ml
Tylosin+Apramycin
25/50+0.8/25=<1
12.5/50+6.25/25=<1
6.25/50+12.5/25=<1

The following antibiotic compositions are preferred compositions
Tylosin—Tobramycin
Tylsoin—Apramycin
Tylosin—Gentamycin
Leucomycin—Tobramycin
Spiromycin—Tobramycin
Magnamycin—Tobramycin Especially preferred compositions are tylosin-tobramycin, tylosin-apramycin, and tylosin-gentamycin.

The antibiotic compositions of this invention are, as described hereinabove, valuable in veterinary medicine in the treatment of various animal diseases. The compositions are also valuable in controlling mycoplasma contamination in the propagation of virus by the tissue culture method.

The following examples further illustrate the present invention.

EXAMPLE 1

Cell suspensions of LLC MK2 (Monkey kidney cell line) in Medium 199 containing 1% house serum of 4 ml volumes in tissue culture flasks were inoculated with a 3 day old culture of *Mycoplasma hyorhinis* ($5 \times 10^8$ organism per ml in Eaton's broth). Approximately 2 to 3% of the mycoplasma culture per volume of the cell suspension was used. After inoculation the cell suspensions were incubated at a temperature of 37° C. for form three to five days. Control cultures were also made up in the same manner. After incubation the medium in the control cultures and the mycoplasma positive cultures was replaced with fresh Medium 199 containing 1.68 g of sodium bicarbonate and 1% horse serum. The cultures were then treated with solutions of tylosin, tobramycin, and with the combination of tylosin and tobramycin in Medium 199 containing 1.68 g of sodium bicarbonate per liter. Solutions of each individual antibiotic and of the combination at a concentration of 1000 mcg/ml were prepared. The solution of the combination had a concentration of each antibiotic of 1000 mcg. By two-fold serial dilution solutions at various concentrations down to 0.39 mcg/ml were prepared. Each of the antibiotic solutions was added to a separate flask containing the tissue culture.

The tissue culture medium was replaced in each flask twice a week and at each medium change for two weeks a fresh solution of the antibiotic at the same concentration was added. After two weeks fresh medium replacements were made for two more weeks without the addition of antibiotic. Samples of each culture were taken before each medium replacement and were cultured to determine the presence of mycoplasma. The minimal inhibitory concentration of the individual antibiotics and of the combination, tylosin and tobramycin, was the lowest concentration of the antibiotic in a given tissue culture which failed to culture for mycoplasma on sampling. The minimum inhibitory concentration for tylosin alone was 100 mcg/ml. and for tobramycin alone was 100 mcg/ml. while for the combination the MIC was 3 mcg/ml.

EXAMPLE 2

When tylosin, apramycin, and the tylosin-apramycin combinations were evaluated in tissue culture contaminated with *M. hyorhinis*. H. H. according to the method and procedures employed as described by Example 1 tylosin alone had an MIC of 200 mcg/ml., apramycin alone had an MIC of 600 mcg/ml. while the tylosin-apramycin combination had an MIC of 12 mcg/ml.

EXAMPLE 3

By employing *M. hyorhinis* in the procedure of Example 1 and substituting gentamicin for tobramycin and tylosin-gentamycin for the tylosin-tobramycin combination, tylosin alone had an MIC of 400 mcg/ml. The combination of tylosin-gentamycin had an MIC of 0.78 mcg/ml.

EXAMPLE 4

The combination, leucomycin-tobramycin, was substituted for the tylosin-tobramycin combination used in Example 1. Leucomycin alone had an MIC of 400 mcg/ml., tobramycin an MIC of 200 mcg/ml. while the combination had an MIC of 0.78 mcg/ml.

We claim:

1. The synergistic antibiotic composition useful for inhibiting the growth of resistant mycoplasma in mammalian tissue cultures comprising the macrolide antibiotic tylosin or a pharmaceutically acceptable salt thereof and the aminoglycoside antibiotic tobramycin or a pharmaceutically acceptable salt thereof in a weight ratio of tylosin to tobramycin or the pharmaceutically acceptable salts thereof of about 12:1 to about 0.5:12.

2. The composition of claim 1 wherein the ratio by weight of tylosin to the tobramycin antibiotic is from about 3:1 to about 1:3.

3. A method for controlling the growth or resistant mycoplasma in mammalian tissue culture which comprises adding to said tissue culture the antibiotic composition of claim 1 in an amount sufficient to achieve a concentration of tobramycin of between about 0.5 mcg/ml and about 12 mcg/ml and a concentration of tylosin of between about 1 mcg/ml and about 12 mcg/ml in said tissue culture.

* * * * *